United States Patent
Rappaport et al.

(10) Patent No.: US 10,416,094 B2
(45) Date of Patent: Sep. 17, 2019

(54) CHARACTERIZATION OF DIELECTRIC SLABS ATTACHED TO THE BODY USING FOCUSED MILLIMETER WAVES

(71) Applicant: Northeastern University, Boston, MA (US)

(72) Inventors: Carey Rappaport, Wellesley, MA (US); Jose A. Martinez-Lorenzo, Wellesley, MA (US); Ann Morgenthaler, Wellesley, MA (US)

(73) Assignee: Northeastern University, Boston, MA (US)

( * ) Notice: Subject to any disclaimer, the term of this patent is extended or adjusted under 35 U.S.C. 154(b) by 60 days.

(21) Appl. No.: 15/462,570

(22) Filed: Mar. 17, 2017

(65) Prior Publication Data
US 2017/0284945 A1  Oct. 5, 2017

Related U.S. Application Data

(60) Provisional application No. 62/316,002, filed on Mar. 31, 2016.

(51) Int. Cl.
*G01N 22/00* (2006.01)
*G01S 13/88* (2006.01)
(Continued)

(52) U.S. Cl.
CPC ............. *G01N 22/00* (2013.01); *G01B 15/02* (2013.01); *G01S 13/887* (2013.01); *G01V 8/005* (2013.01)

(58) Field of Classification Search
CPC ...... G01N 22/00; G01S 13/887; G01B 15/02; G01B 11/02; G01B 11/06; G01B 11/08
See application file for complete search history.

(56) References Cited

U.S. PATENT DOCUMENTS

6,061,583 A * 5/2000 Ishihara ............. A61B 5/14535
                                                    600/322
6,873,860 B2   3/2005 Hildebrand
(Continued)

OTHER PUBLICATIONS

Extended European Search Report for EP 17 16 1767 dated Aug. 31, 2017 entitled "Characterization Of Dielectric Slabs Attached To The Body Using Focused Millimeter Waves".

(Continued)

*Primary Examiner* — Walter L Lindsay, Jr.
*Assistant Examiner* — Milton Gonzalez
(74) *Attorney, Agent, or Firm* — Hamilton, Brook, Smith & Reynolds, P.C.

(57) ABSTRACT

A system for characterizing a dielectric object situated adjacent to an electrically conductive surface comprises a radiation source configured to radiate electromagnetic energy toward the dielectric object, and a receiver configured to receive scattered electromagnetic energy scattered by the dielectric object and the electrically conductive surface. The system may further comprise a control subsystem, coupled to the radiation source and the receiver, that determines an apparent focal point within the object, determines a phase shift associated with the scattered electromagnetic energy with respect to the electromagnetic energy radiated by the radiation source, and determine a thickness and an index of refraction of the object based, on the apparent focal point and the phase shift. The system may determine the apparent focal point by scanning a calculated focus point of the radiated energy through different depths of the object, and searching for a peak in an amplitude of the scattered energy.

20 Claims, 11 Drawing Sheets

(51) Int. Cl.
*G01B 15/02* (2006.01)
*G01V 8/00* (2006.01)

(56) References Cited

U.S. PATENT DOCUMENTS

| | | | |
|---|---|---|---|
| 7,583,221 B2 | 9/2009 | Detlefsen | |
| 7,609,196 B2 | 10/2009 | Jeck | |
| 7,710,307 B2 | 5/2010 | Weinzierl | |
| 7,729,727 B2 | 6/2010 | Jeck | |
| 8,169,355 B2 | 5/2012 | Bartscher | |
| 8,390,504 B2 | 3/2013 | Abdillah | |
| 8,624,772 B2 | 1/2014 | Jeck | |
| 8,670,021 B2 * | 3/2014 | Kuznetsov | G01S 13/867 348/43 |
| 8,760,175 B2 * | 6/2014 | Ostwald | G01S 7/411 324/642 |
| 8,841,618 B2 | 9/2014 | Jeck | |
| 8,897,599 B2 | 11/2014 | Abdillah | |
| 8,946,641 B2 | 2/2015 | Smith | |
| 9,086,483 B2 | 7/2015 | Karam | |
| 9,282,258 B2 * | 3/2016 | Kuznetsov | H04N 5/30 |
| 2006/0002323 A1 | 1/2006 | Hildebrand | |
| 2006/0171345 A1 | 8/2006 | Hildebrand | |
| 2011/0102235 A1 | 5/2011 | Abdillah et al. | |
| 2014/0070111 A1 * | 3/2014 | Rappaport | G01N 23/083 250/395 |
| 2014/0348294 A1 | 11/2014 | Jeck | |
| 2014/0348295 A1 | 11/2014 | Jeck | |
| 2015/0060673 A1 | 3/2015 | Zimdars | |
| 2015/0250388 A1 | 9/2015 | Arbabian et al. | |

OTHER PUBLICATIONS

Weatherall, J.C., et al., "Spectral Signatures for Identifying Explosives With Wideband Millimeter-Wave Illumination", IEEE Transactions on Microwave Theory and Tehniques, vol. 64, No. 3, Mar. 3, 2016.

* cited by examiner

CHARACTERIZATION OF DIELECTRIC SLABS ATTACHED TO THE BODY USING FOCUSED MILLIMETER WAVES

RELATED APPLICATION

This application claims the benefit of U.S. Provisional Application No. 62/316,002, filed on Mar. 31, 2016. The entire teachings of the above application are incorporated herein by reference.

GOVERNMENT SUPPORT

This invention was made with government support under grant number 505081 from The Department of Homeland Security. The government has certain rights in the invention.

BACKGROUND

As people enter secure areas, it is important that they be scanned to ensure that they are not entering with weapons or explosives. In addition to airport departure gates, office buildings, stadiums and other such venues must have fast, accurate, non-intrusive means of detecting threats concealed under a person's clothing.

Portal-based screening systems at security check points may use millimeter wave technology to image objects concealed beneath clothing on a human body. Specific characterization of weak dielectric threat objects, however, is a challenge for millimeter-wave scanning systems. Currently deployed focused mm-wave systems do not specifically address dielectric material. Dielectric slabs appear as anomalies on the body, but are uncharacterized. The inability to accurately characterize dielectric materials with millimeter-wave scanning systems may result in an unacceptable number of false alarms. A false alarm may lead to time-consuming investigative procedures such as pat-downs and other undesirable measures.

SUMMARY OF THE INVENTION

The described embodiments present a system for, and method of, characterizing a dielectric object that is situated on or in close proximity to the skin surface of a human body.

In order to characterize non-metallic, weak dielectric objects (e.g., explosives) on the surface of a highly conducting background (e.g., human skin) using a focused, single-frequency millimeter wave sensor, it is useful to consider distortion of the focusing caused by the dielectric objects. In particular, a slab of penetrable dielectric material will refract focused rays, shifting the apparent focal point. By associating this shift for the specific focus at the dielectric/background interface and by measuring the characteristic phase shift relative to focusing on the background without the dielectric, it is possible to determine—with a single measurement—both the thickness and the permeability of the slab.

This approach can be extended to targets in which the air-dielectric and dielectric-metal interfaces are not parallel. In particular, a traditional non-linear inverse problem can be accurately linearized when the following information is taken into consideration: 1) the total field inside the dielectric object is very close to the incident field (Born approximation); and 2) the dielectric object is backed by a highly conductive scatter (metal plane or human skin). The use of multiple non-focused incident fields may also be used in order to enhance the accuracy of the extracted dielectric constant and thickness.

One example distinguishing factor with a focused single frequency system, as compared to wideband radar, is that the travel time of the Fourier Transform impulse is not available, nor can scattering from different distances be separated in time. For example, in a focused system, the reflection of waves from the front surface of a dielectric slab cannot be observed in isolation without the much stronger scattering from the ground plane a few centimeters behind it. However, focused systems have the advantage of precise phase measurements, a characteristic that is usually neglected in existing sensing systems.

An example embodiment of the present invention capitalizes on this unique configuration by making use of an apparent focal point in penetrable dielectric material, coupled with the measured phase shift of waves relative to skin without the dielectric.

Embodiments of the invention may characterize penetrable dielectrics on skin by considering the refraction and refocusing of rays as they enter the dielectric. Embodiments may provide thickness and dielectric constant of slabs of electromagnetically penetrable media.

In one aspect, the invention is a system for characterizing a dielectric object situated adjacent to an electrically conductive surface. The system may comprise a control subsystem arranged to operate in conjunction with a radiation source. The radiation source may be configured to radiate electromagnetic energy toward the dielectric object. The control system may also be configured to operate in conjunction with a receiver. The receiver may be configured to receive scattered electromagnetic energy that is scattered by the dielectric object and the electrically conductive surface.

The control subsystem may comprise a processor and a memory with computer code instructions stored thereon, with the memory operatively coupled to the processor. The control system may be configured to determine an apparent focal point within the dielectric object, determine a phase shift associated with the scattered electromagnetic energy with respect to the electromagnetic energy radiated by the radiation source, and determine a thickness of the object and an index of refraction of the object based on the apparent focal point and the phase shift. The radiation source may be a continuous-wave millimeter-wave source, or other continuous-wave source capable of emitting electromagnetic energy characterized by a frequency or frequencies, an amplitude, and other parameters descriptive of radiated electromagnetic energy.

The control system may cooperate with an antenna subsystem configured to focus the radiated electromagnetic energy at, within, or proximate to the dielectric object, and to receive the scattered electromagnetic energy scattered by the dielectric object. The antenna subsystem may comprise a Fresnel reflector aperture antenna. The antenna subsystem may include components capable of facilitating the focusing of the radiated electromagnetic energy.

The control subsystem may be configured to adjust a calculated focus point of the radiated energy to scan through different depths of the dielectric object, and to search for a peak in the amplitude of the scattered electromagnetic energy. The control subsystem may be further configured to determine a conductive surface location by scanning the calculated focus point away from the dielectric object (i.e., to a point on the conductive skin surface not occluded, and to determine a distance from the conductive surface location to the apparent focal point.

The control subsystem may produce a thickness determination as object thickness $$= \frac{c\Delta\Phi\Delta F}{c\Delta\Phi + 2\pi f \Delta F}.$$

The control subsystem may produce an index of refraction determination as object index of refraction=

$$= \frac{-c\Delta\Phi}{2\pi f \Delta F}.$$

The control subsystem may determine that an air-to-dielectric interface of the dielectric object is one of (i) parallel to the electrically conductive surface adjacent to the dielectric object and (ii) non-parallel to the electrically conductive surface. When the air-to-dielectric interface of the dielectric object is determined to be non-parallel to the electrically conducting surface, the control subsystem may perform an evaluation of the scattered electromagnetic energy as an iterative solution of:

$$E_s(r, \omega) = \int_{r' \in V} G_b(r, \omega) k_b^2 E_T(r', \omega) \chi(r') dr'.$$

In another aspect, the invention is a method of characterizing a dielectric object situated adjacent to an electrically conductive surface, comprising determining an apparent focal point within the dielectric object, determining a phase shift associated with the scattered electromagnetic energy with respect to the electromagnetic energy radiated by the radiation source, and determining a thickness of the object and an index of refraction of the object based on the apparent focal point and the phase shift. The method may be performed by a processor and a memory with computer code instructions stored thereon. The processor and memory may operate in conjunction with a radiation source that radiates electromagnetic energy toward the dielectric object, and in conjunction with a receiver that receives scattered electromagnetic energy scattered by the dielectric object and the electrically conductive surface. The memory may be operatively coupled to the processor such that, when executed by the processor, the stored computer code instructions cause the system to implement the steps of the method.

The method may further comprise causing the radiated electromagnetic energy to be focused at, within, or proximate to the dielectric object, and to receive the scattered electromagnetic energy scattered by the dielectric object.

The method may further comprise determining the apparent focal point by adjusting (or causing) a calculated focus point of the radiated energy to scan through different depths of the dielectric object, and searches for a peak in an amplitude of the scattered electromagnetic energy.

In another aspect, the invention is non-transitory computer-readable medium with computer code instruction stored thereon. The computer code instructions, when executed by an a processor, cause a dielectric object detection system to determine an apparent focal point within the dielectric object, based on electromagnetic energy scattered by the dielectric object and the electrically conductive surface, determine a phase shift associated with the scattered electromagnetic energy with respect to the electromagnetic energy radiated by the radiation source, and determine a thickness of the object and an index of refraction of the object based on the apparent focal point and the phase shift. The computer code instructions, when executed by an a processor, may further cause a dielectric object detection system to adjust a calculated focus point of the radiated energy to scan through different depths of the dielectric object, and search for a peak in an amplitude of the scattered electromagnetic energy.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1:
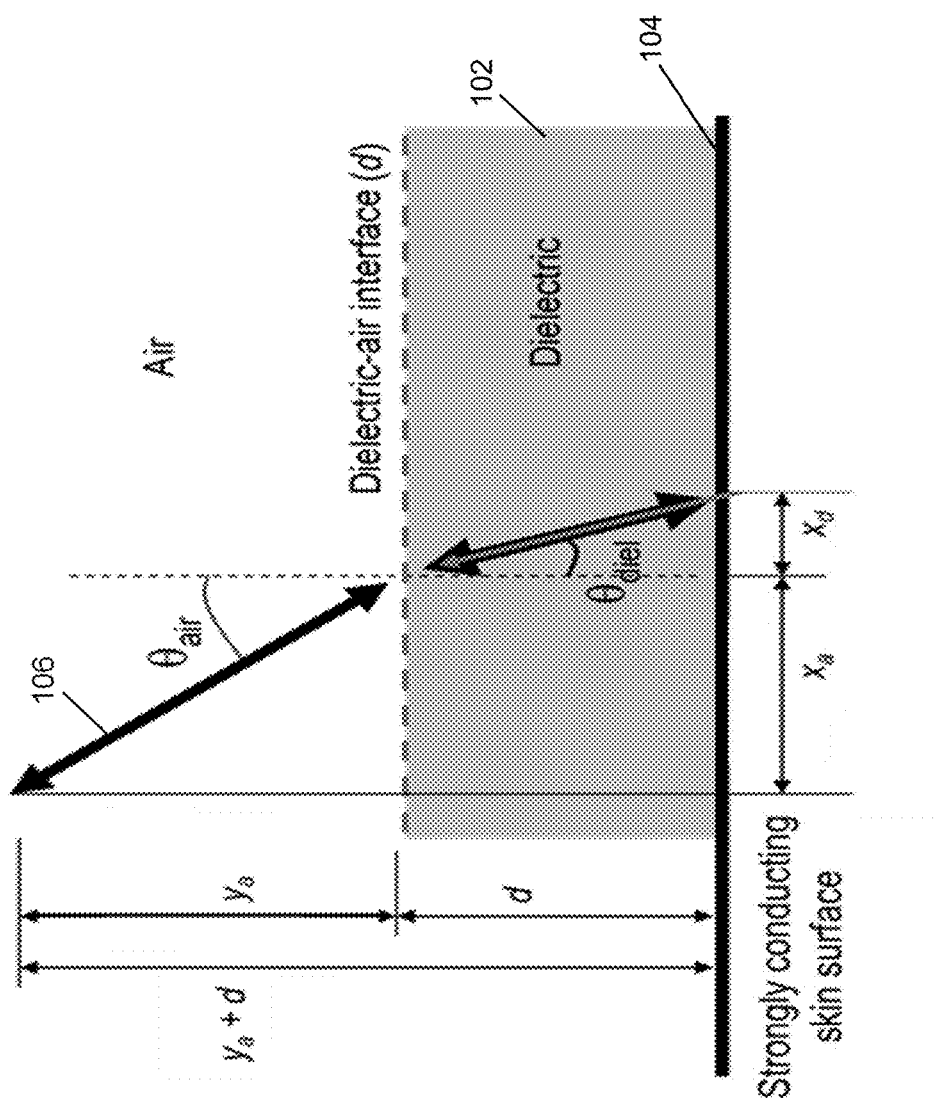
FIG. 1 illustrates a geometry of a dielectric slab on a strongly reflecting skin surface.

Consider the idealized geometry of a dielectric slab 102 of thickness d on a strongly reflecting skin surface 104, as shown in FIG. 1. A ray 106 incident at angle $\theta_{air}$ refracts in material with index of refraction n according to Snell's Law ($n \sin \theta_{diel} = \sin \theta_{air}$), ending toward the surface normal.

Figure 2:
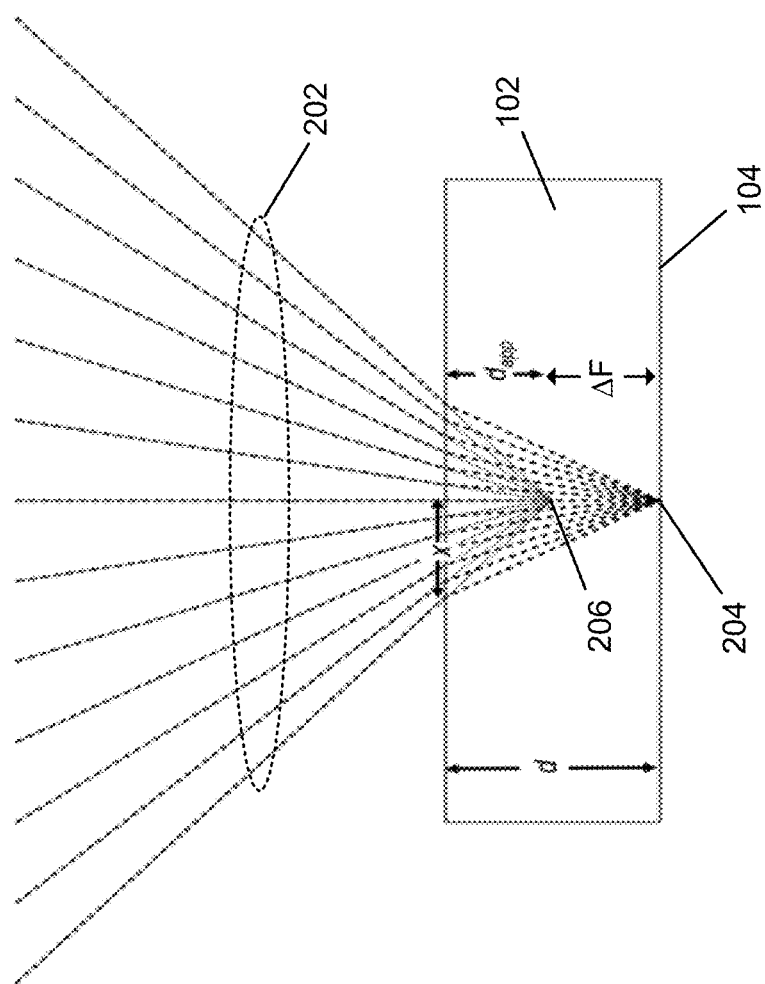
FIG. 2 illustrates a collection of rays focused to a point within the dielectric of FIG. 1.

FIG. 2 illustrates that a collection of rays 202 focused to a point within the dielectric 102 are all bent (except for the normal ray), and that the true focal point 204 is deeper than the apparent focal point 206 (i.e., the focal point that would occur without the dielectric). The ratio of horizontal position of the refraction point x, to the vertical distance d of the true focal point 204 is $\tan \theta_{diel}$, and the corresponding ratio for the apparent vertical distance $d_{app}$ is $\tan \theta_{air}$. For rays close to normally incident, $\theta_{diel}$ and $\theta_{air}$ are small, and $$\tan\theta_{diel} \approx \sin\theta_{diel} = \frac{1}{n}\sin\theta_{air} \approx \frac{1}{n}\tan\theta_{air},$$

which results in the simple relation $$d_{app} \approx \frac{d}{n}.$$

This means that for rays focused at a point at depth d below the air/dielectric interface, the apparent focusing point 206 of an antenna generating these rays is at a depth $d_{app}$. That is, if it is desired to focus on the skin surface under a dielectric slab of thickness d, the antenna system should instead focus at the point above the skin 104 having a y component of:

$$y = d\left(1 - \frac{1}{n}\right)$$

This apparent focusing effect has been modeled using axi-symmetric finite-difference frequency-domain (FDFD) for focused rings of x-directed current elements discretized into 0.0075 m steps for 24 GHz. The focused source is $y_a+d=0.40$ m from the nominal skin interface, with a maximum ring radius of 0.40 m. A half space of dielectric with the index of refraction of the explosive TNT (n=1.73) occupies the space below y=0.03 m (corresponding to a slab with thickness d=3 cm). Focusing on the apparent focal point 206 with a y component of y=d (1−1/n)=0.0127 m produces an electric field high-intensity spot very close to y=0, the true focal point 204. This model does not include the skin ground plane, as the reflection would cancel the z-directed electric field at y=0. The response from the skin surface for with the focal point y=ΔF=d(1−1/n)=0.0127 m would be comparable to the response form the skin surface in the case with no dielectric, focusing at y=0 (i.e., directly at the skin surface).

Waves passing through a slab of dielectric experience a phase shift. The extra phase in terms of frequency f is given by:

$$\Delta\Phi = \frac{2\pi f}{c}d(1-n), \quad (A1)$$

where c is the velocity of propagation of the radiated EM energy. For the example presented above, the phase shift ΔΦ is 11.04 radians. This phase shift ΔΦ is significant, and straightforward to measure at a receiver of the scattered electromagnetic energy associated with the radiating source. The values of index of refraction n and slab thickness d are given by:

$$n = \frac{-c\Delta\Phi}{2\pi f \Delta F} \quad (A2)$$

$$d = \frac{c\Delta\Phi\Delta F}{c\Delta\Phi + 2\pi f \Delta F} \quad (A3)$$

The permeability of the dielectric slab 102 may be determined from the index of refraction n, as $=\sqrt{\varepsilon\mu}$. Assuming that the permittivity of the dielectric is approximately $\mu_0$, the dielectric permeability $\varepsilon = n^2/\mu_0$.

An example scanning system according to the described embodiments may determine ΔF by calculating an apparent focal point 206 based on EM transmitter and antenna settings, varying those settings to scan the apparent focal point 206 through the dielectric slab 102, and identifying apparent focal point depths that result in a relative increase in returned electromagnetic energy. Such an increase may correspond to scattering due to an actual focal point occurring at the skin boundary 104.

Figure 3:
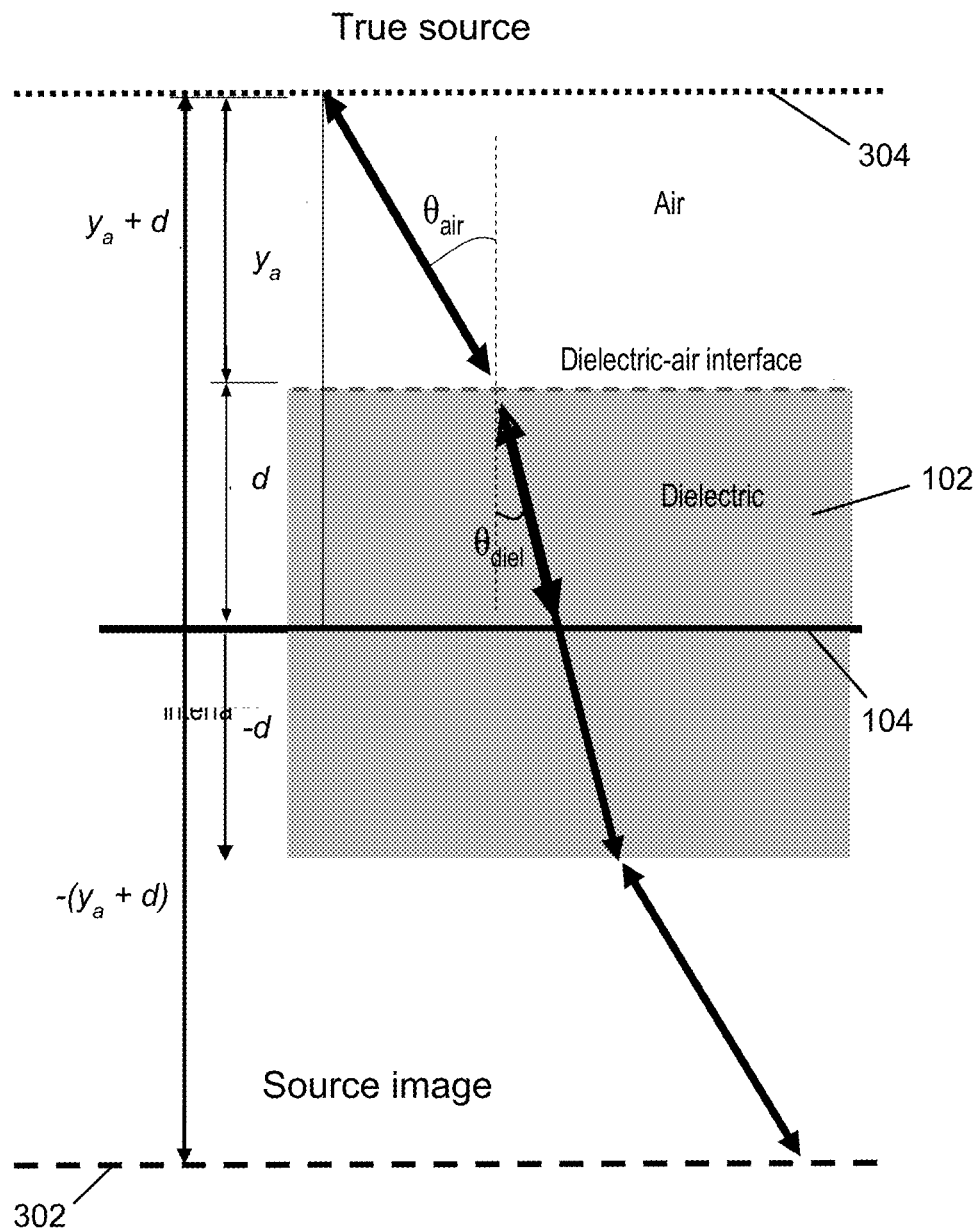
FIG. 3 shows image information replacing the reflecting, conductive skin of FIG. 1.

Since a maximum scattering return may be employed to determine ΔF, it is useful to determine the focal distributions which may yield returns at or approaching a maximum received signal. Referring to FIG. 3, since a planar conducting skin surface 104 acts like a perfect conductor, which generates an equal and opposite image source 302 at a position of $y=-(y_a-d)$, the received signal is not maximized when the source 304 (i.e., the transmitting and receiving antennas) are focused on the skin surface 104. Instead, the signal is maximized when the source 304 antennas are focused at the plane of the image source 302. Thus, for skin with no dielectric, the image should focus at $y=-(y_a+d)$, with a corresponding focal length of $2(y_a+d)$, as indicated in FIG. 3, and considering the dielectric to be free space.

To maximize the received signal when a layer of dielectric is present, it is necessary to compute the path length from the image source through a double thickness of dielectric (slab plus its image), back to the receiving antenna. The differential path length through the 2d thickness of dielectric with refractive index n is:

$$\Delta p_{imag} = -2d\left(1 - \frac{1}{n}\right),$$

which makes the focal length:

$$F = 2y_a + \frac{2d}{n}.$$

The description below presents a fast, non-iterative model based on a ray tracing analysis, associate with the embodiments described herein, for characterizing the thickness and refractive index of a dielectric slab.

The millimeter wave transmit/receive system can be modeled in two dimensions by an array of point sources with adjusted phase along a horizontal line above the ground plane on which the dielectric sits. It is assumed that the array has the same phase adjustment on transmission and reception, and that the dielectric is ideal and has unknown thickness and permittivity.

When a focused wave is sent from the transmitter array toward the dielectric slab, it will scatter from two interfaces; the ground plane interface at the dielectric bottom surface, and the dielectric/air interface at the dielectric top surface. Neglecting additional scattered fields inside the dielectric, five dominant scattering phenomena emerge from this model with three material constant interfaces; at the true air/dielectric interface, the air/dielectric image interface, the ground plane, and their associated reflections.

Figure 4:
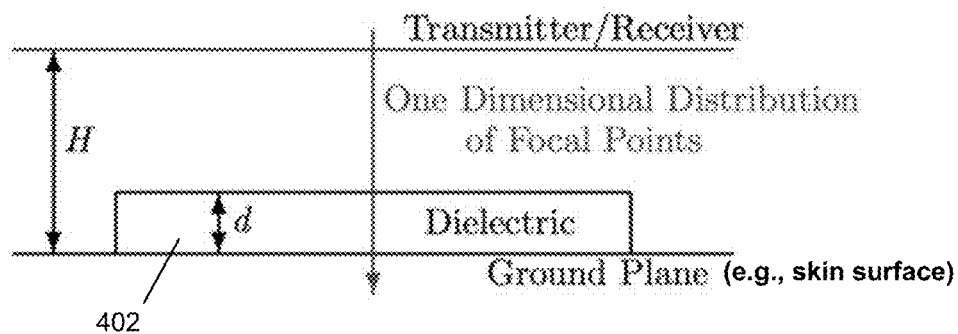
FIG. 4 illustrates an alternative view of a dielectric slab on a strongly reflecting skin surface.

FIG. 4 shows a slab 402 of dielectric of thickness d on top of a metal ground plane and a horizontal transmitter/receiver array located at a distance H above the ground; the transmitter array focuses to different depths into the air and the dielectric. Considering the image of the dielectric and antenna array relative to the metal ground plane, there will be three scattering interfaces. By limiting the scattering at interfaces to single points along the range axis generated using a focused one-dimensional array, one can straightforwardly predict what the received signal should look like from a given dielectric thickness and refractive index.

Figure 5:
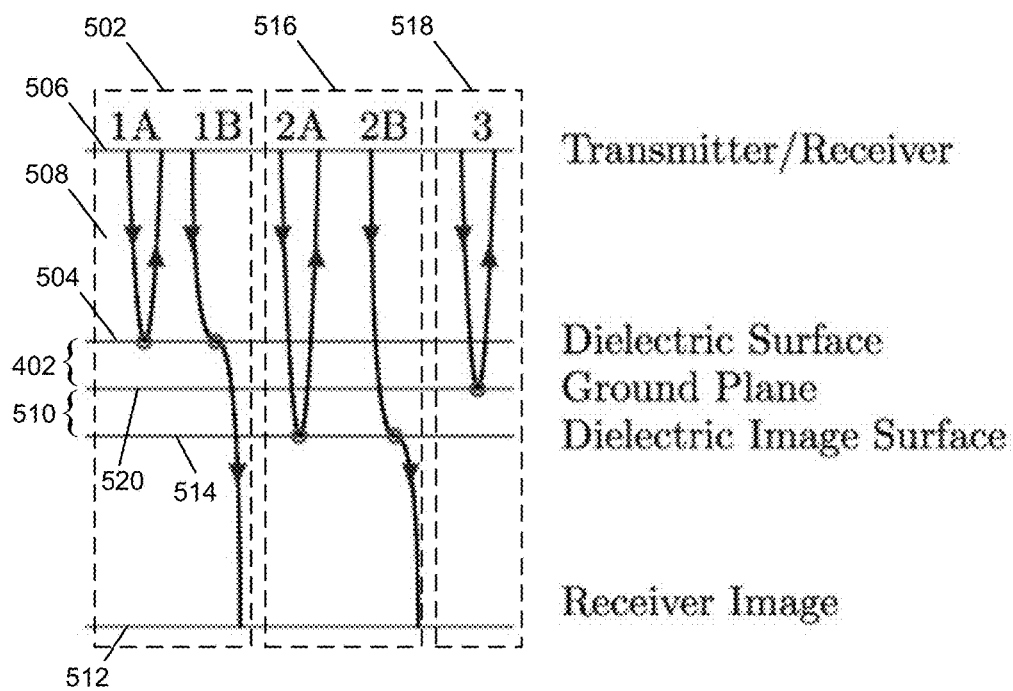
FIG. 5 shows various scattering phenomena related to the arrangement of FIG. 4.

Considering only the first reflection, from the dielectric top surface or its image, FIG. 5 shows the five scattering phenomena to be considered. In the first case 502, scattering occurs at the top surface 504 of the dielectric 402. The rays scatter back to the receiving array 506 (Case 1A) and forward into the dielectric 402 (Case 1B). In Case 1A, the path travels only through the air 508, with the same path length on transmission and reception. This received signal is scaled by the scattering cross-section, approximated by the reflection coefficient of the dielectric 402, about −0.25.

In Case 1B, using image theory to analyze the ray paths, the images 510 of the dielectric slab image 510 and receiving array image 512 replace the ground plane. The transmitted rays now begin at the source, scatter at the dielectric/air interface 504, pass through the double wide dielectric slab 402 and 510, refract from inside at the image interface 514 (with intensity multiplied by the transmission coefficient), and finally point to the receiver array image 512.

In the second case 516, the scatterer is located at the image interface 514 of the dielectric; rays refract through the true dielectric surface 504 to scatter at this point. Again, contributions to the signal come from both backscatter (Case 2A) and forward scattering (Case 2B) at the image interface 514. In Case 2A, the backscattered rays refract back through the true dielectric surface 504 and return to the true receiver array 506; in Case 2B the forward scattered rays travel through air to the image receiver array 512. Note that the scattering at the image interface 514 of the dielectric/air interface has a coefficient based on the material contrast that is equal and opposite to the scattering coefficient of Case 1A above.

With a scatterer at the ground plane for the third case 518, the signal reflects from the ground plane 520 back to the receiver array with no image involved. The ray paths into and out of the dielectric are refracted, and the transmission coefficient must be applied for each refraction.

The coherent addition of all these signals (with appropriate choice of wavenumber k), for Cases 1A, 1B, 2A, 2B, and 3, gives the final signal received by the receiving array 506.

For Cases 1A, 2A, and 3, the backscattered paths are the same as the incident paths, so one would expect strong responses for these scattering phenomena. For Cases 1B and 2B, the forward scattered paths are different from the incident paths, so these cases will be relatively incoherent and unfocused for the sensing system.

Figure 6:
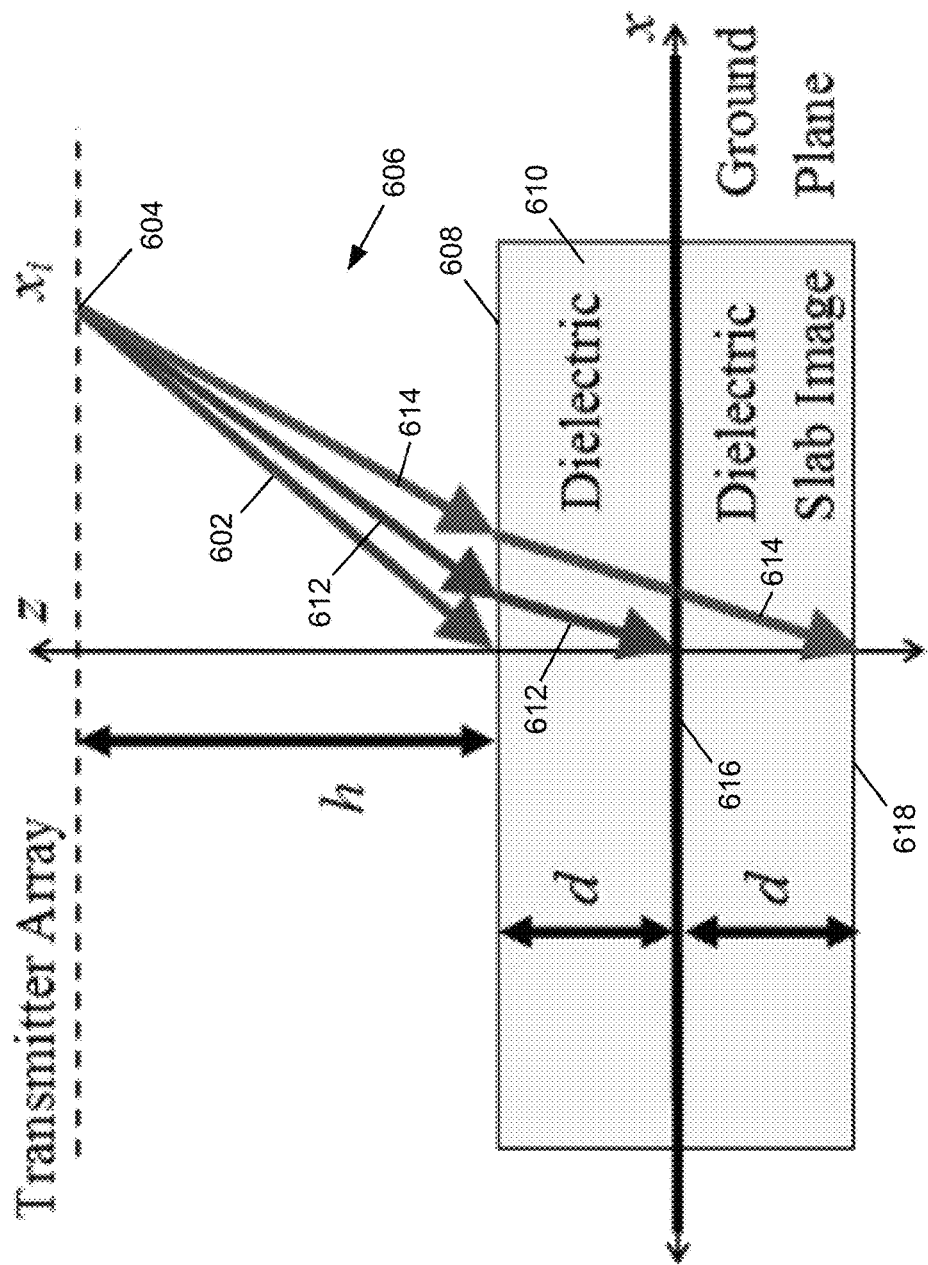
FIG. 6 illustrates various path lengths associated with a signal radiated at a dielectric slab such as shown in FIG. 4.

Mathematically, there are several path lengths to compute for each contribution to the signal, as depicted in FIG. 6. The first path 602 is the distance from a particular transmitter 604, through the air 606, to the surface 608 of the dielectric slab 610 at (0, d). The first path 602, denoted $r_1$, is given by:

$$r_1 = \sqrt{x_i^2 + h^2}, \tag{1}$$

where $x_i$ is the horizontal distance from a particular transmitter to the central axis, h is the distance from the transmitter array to the dielectric slab, and d is the thickness of the slab.

In FIG. 6, the second path 612 (denoted $r_2$) and the second path 614 (denoted $r_3$) are the reflected paths of rays when the array is configured as if to focus at points inside of the dielectric 610. The rays refract to hit the ground plane 616 and image surface 618 at distances d and 2d below the top dielectric surface 608.

Figure 7:
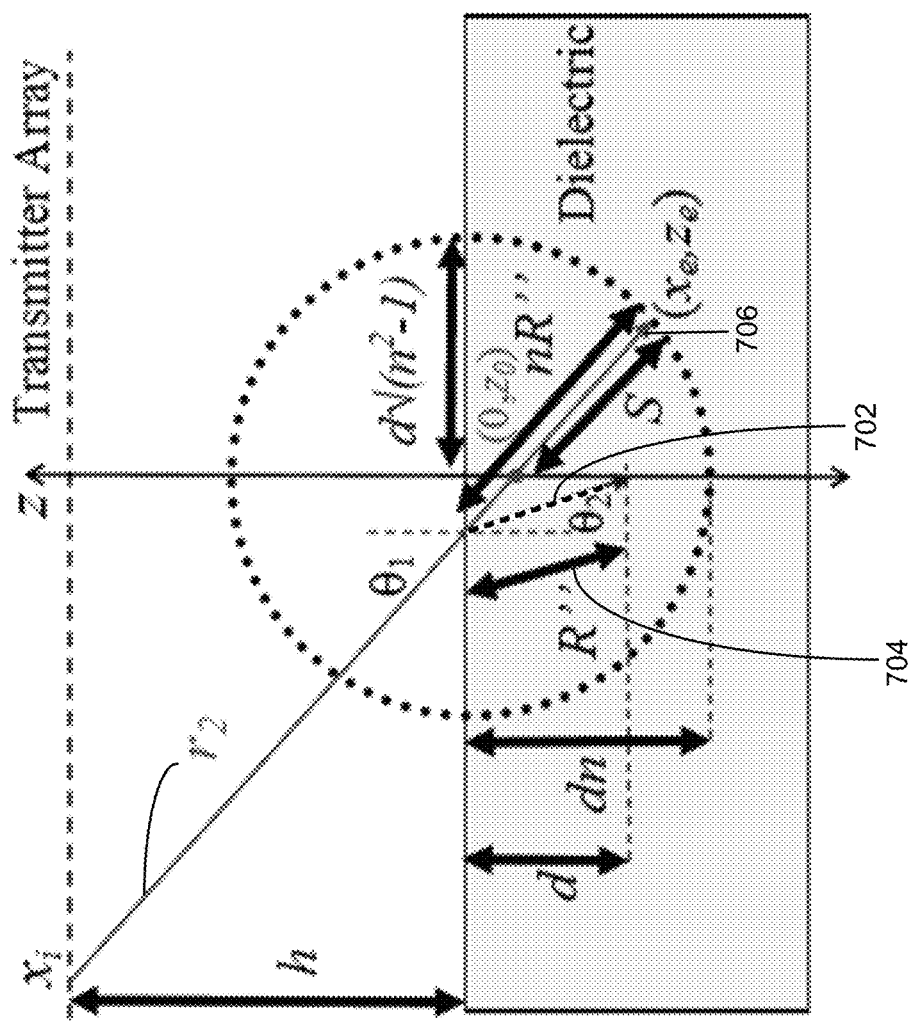
FIG. 7 shows a ray diagram related to the paths illustrated in FIG. 6.

Referring to FIG. 7, the electric path length 702 traveled inside the dielectric (the dashed path in FIG. 7) is given by nR", where R" 704 is the physical distance traveled inside the dielectric and n is the refractive index of the dielectric. This electrical distance is equivalent to the physical distance nR" for a ray continuing through air instead, shown by the ray 706 extending below z=d.

The extended ray 706 ends at a point $(x_e, z_e)$. For rays starting from different points $x_i$, there are different $(x_e, z_e)$ points, but all of these points lie on an ellipse given by equation (2) below:

$$\left(\frac{x_e}{d\sqrt{n^2-1}}\right)^2 + \left(\frac{z_e}{dn}\right)^2 = 1 \tag{2}$$

The path length can be found by taking the distance from $(x_i, h)$ to $(x_e, z_e)$:

$$r_2 = \sqrt{(x_i - x_e)^2 + (h - z_e)^2} \tag{3}$$

Moreover, the line between the two points $(x_i, h)$ and $(x_e, z_e)$ is normal to the ellipse, implying:

$$x_i = x_e + (h - z_e)\frac{n^2 x_e}{(n^2 - 1)z_e} \tag{4}$$

Substituting $x_i$ from equation (4) and $x_e$ from equation (2) into the path equation and simplifying, gives:

$$r_2 = \frac{(h - z_e)}{z_e}\sqrt{\frac{d^2 n^4 - z_e^2}{n^2 - 1}} \tag{5}$$

The values of $r_2$ and $x_i$ in equations (4) and (5) can be plotted parametrically against each other in terms of $z_e$. This complicated relationship between r and $x_i$ can be approximated very closely by a simpler equation for path in terms of x:

$$r_2 \approx \sqrt{x_i^2 + (h - z_0)^2} + S \tag{6}$$

where S and $z_0$ are constants; $-z_0$ is the depth below the air/dielectric interface corresponding to the array focal point in air which produces the true focus in dielectric at the depth d, and S is the phase offset that compensates for the extra path length to the more distant focal point. Note that in terms of previously used variables, $z_0 = \Delta F - d$. The approximation in equation (6) can be made by choosing two points along the parametric curve of $x_i$ and $r_2$ (for example, $z_e = -d$ n and $z_e = -p$ d n, where p is the fitting parameter between 0 and 1), inserting them into (6), and solving for $z_0$ and S. These values for S and $z_0$ can be substituted into equation (6) to find the approximate path length formula as a function only of antenna position $x_i$:

$$S = -1/2 \frac{d(-1 + p)(2hn + dp(1 + p))}{-p(h + dn) + (h + pdn)\sqrt{\frac{(n^2 - p^2)}{(-1 + n^2)}}} \tag{7}$$

and $$z_0 = -dn + S, \tag{8}$$

which are more accurate calculations than those of equations (A1), (A2) and (A3) presented herein, although either of the calculations may be used in the described embodiments.

To find $r_3$, the path length to the image dielectric surface, the ellipse method can again be used, substituting 2d for d, as the dielectric and its image form a slab with twice the thickness.

Figure 8:
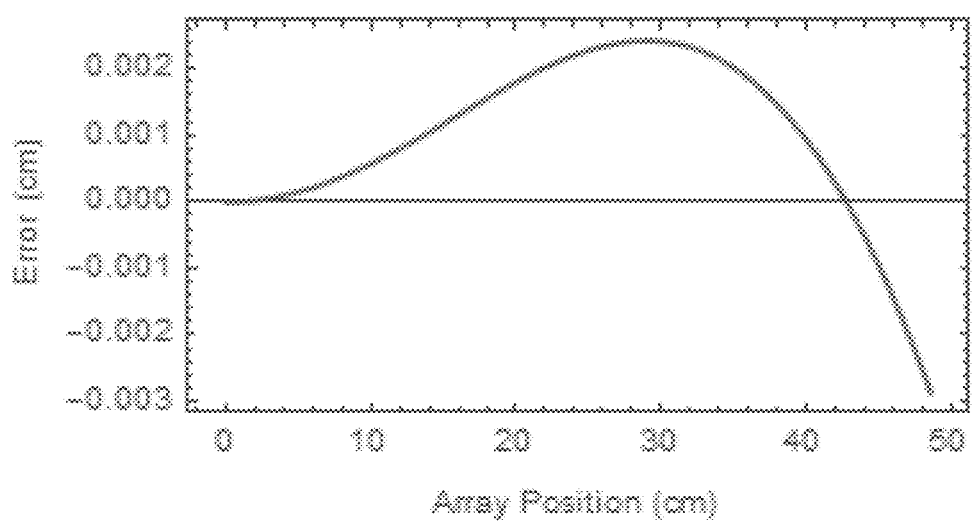
FIG. 8 shows a graph plotting error with respect to array position.

For example, for array distance h=80 cm, array width $2x_i$=100 cm, dielectric slab thickness d=3.7 cm, and index of refraction n=1.73, the fitting parameter can be chosen to be p=0.92. The parametric equation in terms of $z_e$ and the approximation in terms of S=4.34 and $z_0$=−2.05 match almost exactly in the desired range of $x_i$. The error of the approximation in this range is less than 0.003 cm, as shown in FIG. 8.

Therefore, using equation (6), the path lengths $r_2$ and $r_3$ can be found simply and accurately in terms of the antenna array position. It is fortuitous that the form of equation (6) is similar to the form for rays focused in air from a linear array. The signal from each component can be calculated given these path lengths. For the various values of r ($r_1$, $r_2$, or $r_3$), the corresponding focused sum $S_1$, $S_2$, $S_3$ is given by:

$$S_n = \sum_{i}^{\text{\#antenna\_elements}} e^{-jkr_{n_i}} * e^{j\phi_i} \quad (9)$$

where k represents the wavenumber and $\Phi$ represents the phase for the $i^{th}$ antenna element.

The total signal from each scattering component can be determined by multiplying the values of $S_n$ on transmission and reception for each scattering case with the appropriate transmission and scattering coefficients:

$$\begin{bmatrix} E_{1a} \\ E_{1b} \\ E_{2a} \\ E_{2b} \\ E_3 \end{bmatrix} = \begin{bmatrix} \Gamma * S_1 * S_1 \\ \Gamma * T_2 * S_1 * S_3 \\ T_1 * (-\Gamma) * T_2 * S_3 * S_3 \\ T_1 * (-\Gamma) * S_3 * S_1 \\ T_1 * T_2 * S_2 * S_2 \end{bmatrix} \quad (10)$$

where $\Gamma$ is the scattering coefficient of the dielectric, and $T_1$=1+$\Gamma$ and $T_2$=1+(−$\Gamma$)

are the transmission coefficients. Scattering from air into dielectric multiplies by a coefficient of $\Gamma$, and scattering from inside the dielectric to air multiplies by −$\Gamma$. Refraction into the dielectric multiplies by a coefficient of $T_1$, while refraction out of the dielectric multiplies by $T_2$.

The most speculative scattering assumption being made with this ray analysis is that the scattering from an interface occurs as if all incident rays were focused at a point on the interface, even when the focal point might be nearby but not exactly on the interface. The scattering from a point scatterer is straightforward to model with rays, and with a focused illumination with all rays converging on a single point on an interface, this is an effective approximation.

Once the focal point leaves the surface, though, the illuminated region of the surface is no longer a small point, and the scattering from the surface is no longer that of a point scatterer. However, if the focal point is not too far from the surface, the rays will still converge, approaching each other with small separation, and their respective phases will be almost the same. The scattering from a single point on the interface will still reasonably represent the scattering from the partially focused spot. The intensity variation of the scattering with distance from the interface will be close to true values past the half-power point, although the side-lobe locations and levels will be inaccurately predicted. For the purposes of identifying locations and pulse widths of the reconstructed signals, this approximation is acceptable.

Extension to Non-Parallel Interfaces

The measured scattered field produced by the geometry described herein is given by:

$$E_s(r, \omega) = \int_{r' \in V} G_b(r, \omega) k_b^2 E_T(r', \omega) \chi(r') dr' \quad (11)$$

Where $E_s(r,\omega)$ represents the scattered field measured by a receiving antenna located at the position r and operating at frequency $\omega$; $G_b$ indicates the background Green's functions; $k_b^2$ is the square of the wave number; $E_T$ is the total field at the slab region $r' \in V$; and $\chi(r')$ is a contrast variable defined as $$\chi(r') = \frac{\varepsilon(r', \omega) - \varepsilon_b(r', \omega)}{\varepsilon_b(r', \omega)}$$

The term $\varepsilon(r',\omega)$ represents the dielectric constant at point r; and the term $\varepsilon_b(r',\omega)$ represents the background dielectric constant.

For our particular problem, the unknown total field is approximated by the known background field $E_T \approx E_b$ (Born approximation valid for weak dielectrics), $G_b$ is known since it accepts an analytical expression for a highly conductive scatter (metal or human skin) in free space, $k_b^2$ is also known for the latter geometry. Therefore the only two unknowns are the support $r' \in V$ for the dielectric slab and the true dielectric constant for the dielectric slab $\varepsilon(r',\omega)$. This problem may be solved in an iterative fashion as follows:

Operation 1—First, initialize $\varepsilon^{(0)}(r',\omega) \approx \varepsilon_w(r',\omega)$, where $\varepsilon_w(r',\omega)$ is a first guess of the dielectric constant (e.g., TNT is approximately equal to 3). Second, linearize equation (11) as $E_s = A\{\varepsilon^{(0)}(r',\omega)\}v^{(0)}$, where $A\{\varepsilon^{(0)}(r',f)\}$ is a matrix that results when the integral operator in (11) is discretized for a known dielectric constant ($\varepsilon^{(0)}(r',\omega)$), and $v^{(0)}$ is just the unknown vector that should provide a "1" if a pixel belongs to the support of the dielectric scatter and "0" if not. Third, invert the matrix and compute $v^{(0)}$.

Operation 2—First, given the known support $v^{(0)}$, discretize (Eq-1) as $E_s = B\{v^{(0)}\}\varepsilon^{(1)}(r',\omega)$, where $B\{v^{(0)}\}$ is the matrix that results when the integral operator in (Eq-1) is discretized for a known support $v^{(0)}$, and $\varepsilon^{(1)}(r',\omega)$ is the unknown true dielectric constant. Third, invert the matrix to compute $\varepsilon^{(1)}(r', \omega)$.

Operation 3—Iterate operations (1) and (2) using, for the $i^{th}$ iteration, the following equations:

$$v^{(i)} = A^{-1}\{\varepsilon^{(i)}(r',\omega)\}E_s$$

$$\varepsilon^{(i+1)}(r',\omega) = B^{-1}\{v^{(i)}\}E_s$$

This method can be solved for one-dimensional, two-dimensional and three-dimensional geometries. Information about dielectric constant and thickness slab derived from the ray-based method described herein can be implemented as an initial operation for this iterative method in order to speed up the convergence and to reduce the potential ill-posedness of the inverse problem.

Figure 9A:
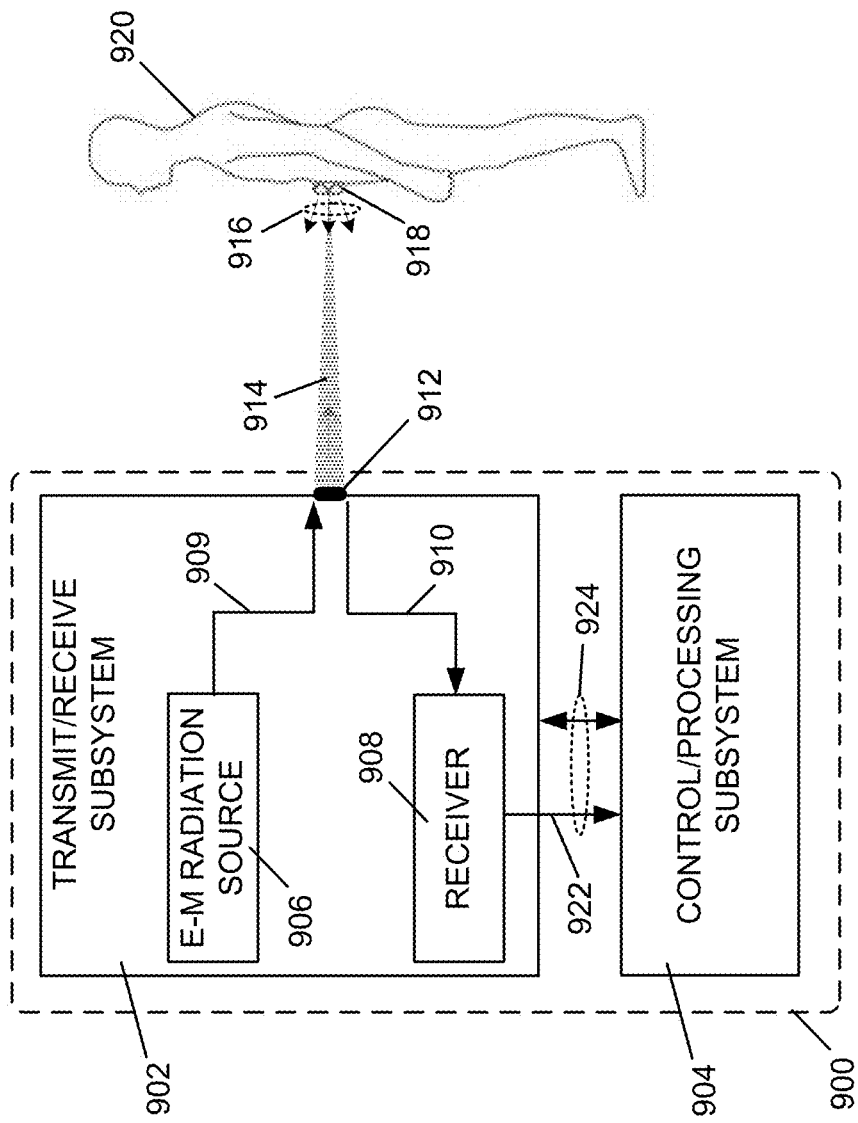
FIG. 9A illustrates an example embodiment of a scanning system employing an embodiment of the invention.

FIG. 9A illustrates an example embodiment of a scanning system 900 according to the described embodiments. The scanning system 900 may be used, for example, as part of a security portal at an airport security checkpoint, although the scanning system 900 may be used in other scenarios requiring object detection or characterization. The scanning system 900 comprises a transmit/receive subsystem 902, and a control/processing subsystem 904. The transmit/receive subsystem may include an electromagnetic (EM) radiation source 906, a receiving subsystem 908, and an antenna assembly 912.

In the example embodiment, the EM radiation source 906 comprises a continuous wave (CW) transmitter producing EM radiation at 24.16 GHz, although EM energy at higher (e.g., into the millimeter wave, Extra High Frequency (EHF) band) or lower frequency may alternatively be used for the described embodiments. The antenna assembly 912 in the example embodiment is a Fresnel reflector aperture, although other antennas and antenna systems capable of focusing CW radiation may alternatively be used.

The example embodiment uses a single antenna assembly 912 for transmitting the CW EM radiation 914 and for receiving the scattered EM fields 916. In other embodiments, the scanning system may utilize separate receive and transmit antennas.

In transmit mode the EM radiation source 906 directs CW EM energy 909 to the antenna 912. The transmitted EM radiation 914 interacts with the potential threat object 918, and the skin of the person 920 against which the object 918 is disposed, to produce the scattered EM fields 916. In receive mode, the receiver 908 receives returned EM energy 910 gathered by the antenna 912 from the scattered EM fields 916.

In operation, the control/processing subsystem 904 controls the transmit/receive subsystem 902 to direct the focal point of the transmitted EM radiation 914 to various depths of the potential threat object 918. The receiver 908 provides derived information 922 from the returned EM energy 910 to the control/processing subsystem 904. The derived information 922 may simply be a frequency-shifted version of the returned EM energy, or the receiver 908 may perform additional processing necessary to render the underlying information suitable for use by the control/processing subsystem. For example, the receiver may determine the phase of the returned EM energy 910, relative to the phase of the transmitted energy, and provide the determined phase information to the control/processing subsystem 904.

The control/processing subsystem 904 monitors the derived information 922, which is based on the returned EM energy 910, to identify relative increases in returned EM energy magnitude. Such magnitude peaks may correspond to the focal point being at or near the dielectric/skin interface, or at the receiver image, as described herein. Using this returned scattering information, the control/processing subsystem may determine the thickness and permeability of the potential threat object 918, based on the focal point location and the phase shift of the returned EM energy 910 relative to the transmitted energy, as described herein. The control/processing subsystem 904 may further compare the determined permeability information to a permeability database of known substances to characterize the potential threat object.

Figure 9B:
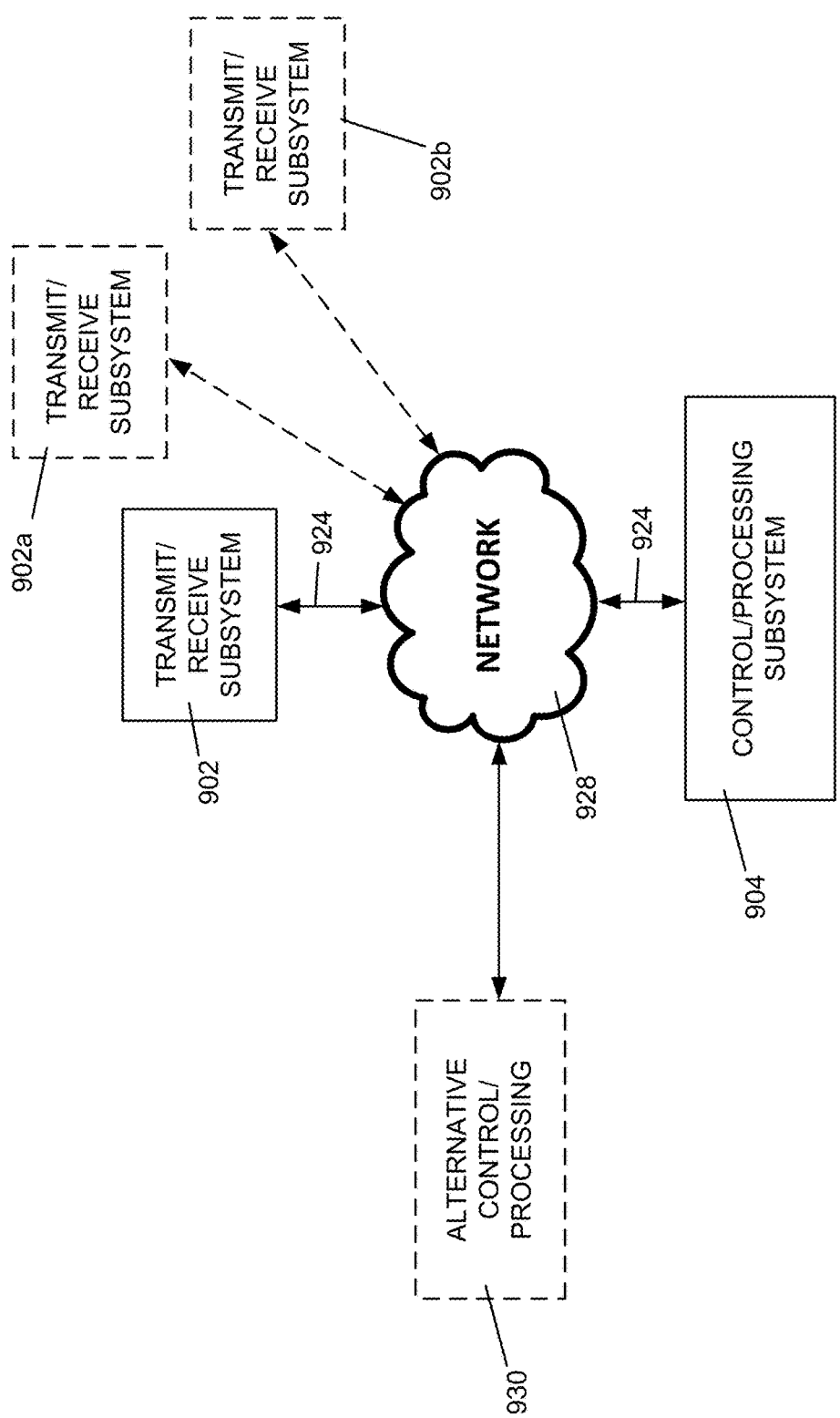
FIG. 9B illustrates an alternative example embodiment of a scanning system employing an embodiment of the invention.

FIG. 9B illustrates an alternative embodiment that separates the transmit/receive subsystem 902 and the control/processing subsystem 904 to different physical locations, so that part of the communications link 924 includes a connection through a network 928. In this embodiment, the control/processing subsystem 904 may operate as a software as a service (SAAS) component. A portion of the control/processing functionality may reside in the transmit/receive subsystem 902, on the transmit/receive subsystem side of the network 928.

Further, the control/processing subsystem may operate to provide processing and control services to more than one transmit/receive subsystems (i.e., 902, 902a and 902b). Such a network-based system may further facilitate the use of an alternative control processing subsystem 930, which may provide certain control/processing services, or may simply receive processing results from one or both of the control/processing subsystem 904 and the transmit/receive system.

Figure 10:
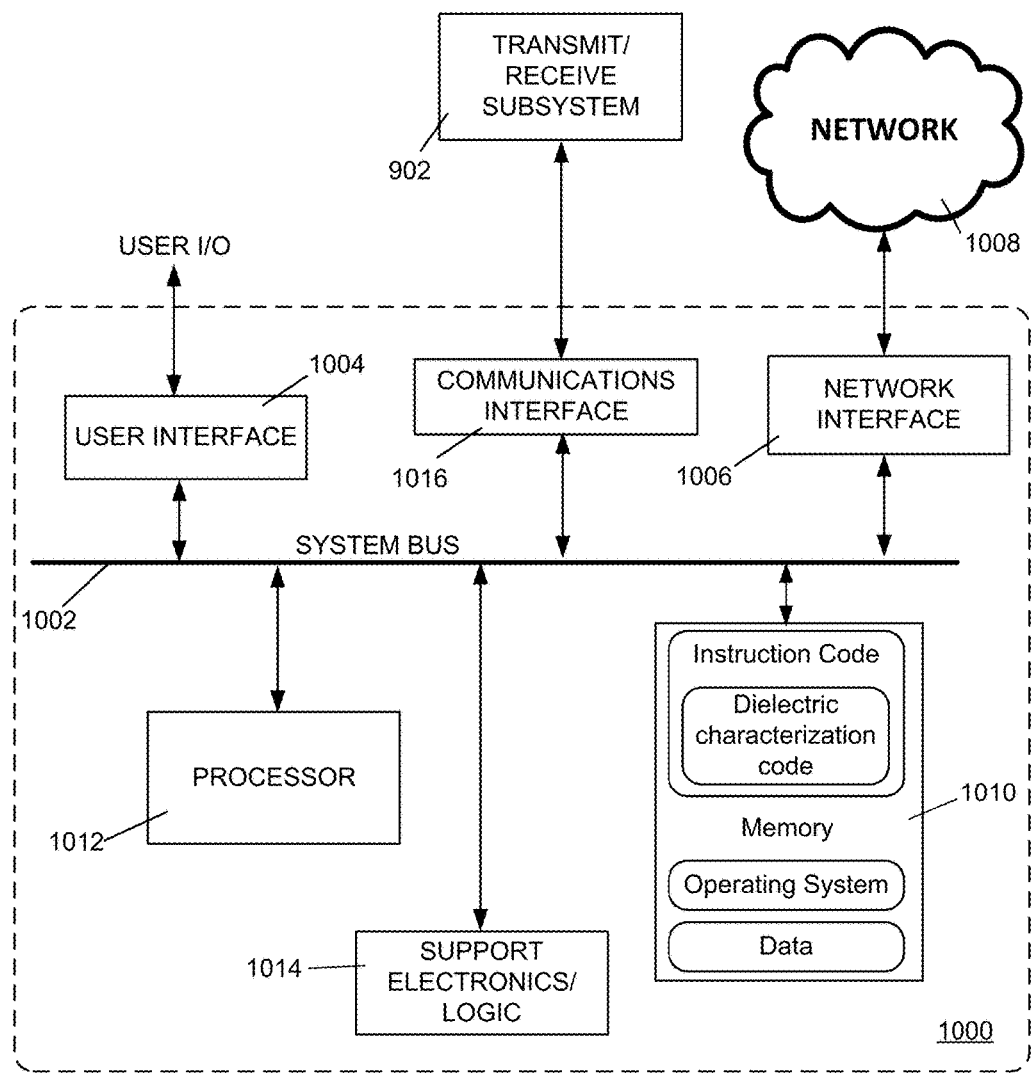
FIG. 10 shows a diagram of an example internal structure of a processing system that may be used to implement one or more of the described embodiments.

FIG. 10 is a diagram of an example internal structure of a processing system 1000 that may be used to implement one or more of the embodiments herein. For example, the control/processing subsystem 904 described with respect to FIG. 9 may comprise a processing system 1000.

Each processing system 1000 contains a system bus 1002, where a bus is a set of hardware lines used for data transfer among the components of a computer or processing system. The system bus 1002 is essentially a shared conduit that connects different components of a processing system (e.g., processor, disk storage, memory, input/output ports, network ports, etc.) that enables the transfer of information between the components.

Attached to the system bus 1002 is a user I/O device interface 1004 for connecting various input and output devices (e.g., keyboard, mouse, displays, printers, speakers, etc.) to the processing system 1000. A network interface 1006 allows the computer to connect to various other devices attached to a network 1008. Memory 1010 provides volatile and non-volatile storage for information such as computer software instructions used to implement one or more of the embodiments of the present invention described herein, for data generated internally and for data received from sources external to the processing system 1000.

A central processor unit 1012 is also attached to the system bus 1002 and provides for the execution of computer instructions stored in memory 1010. The system may also include support electronics/logic 1014, and a communications interface 1016. The communications interface may comprise the communications link 924 between the receiver 908 and the control/processing subsystem 904.

In one embodiment, the information stored in memory 1010 may comprise a computer program product, such that the memory 1010 may comprise a non-transitory computer-readable medium (e.g., a removable storage medium such as one or more DVD-ROMs, CD-ROM's, diskettes, tapes, etc.) that provides at least a portion of the software instructions for the invention system. The computer program product can be installed by any suitable software installation procedure, as is well known in the art. In another embodiment, at least a portion of the software instructions may also be downloaded over a cable communication and/or wireless connection.

Figure 11:
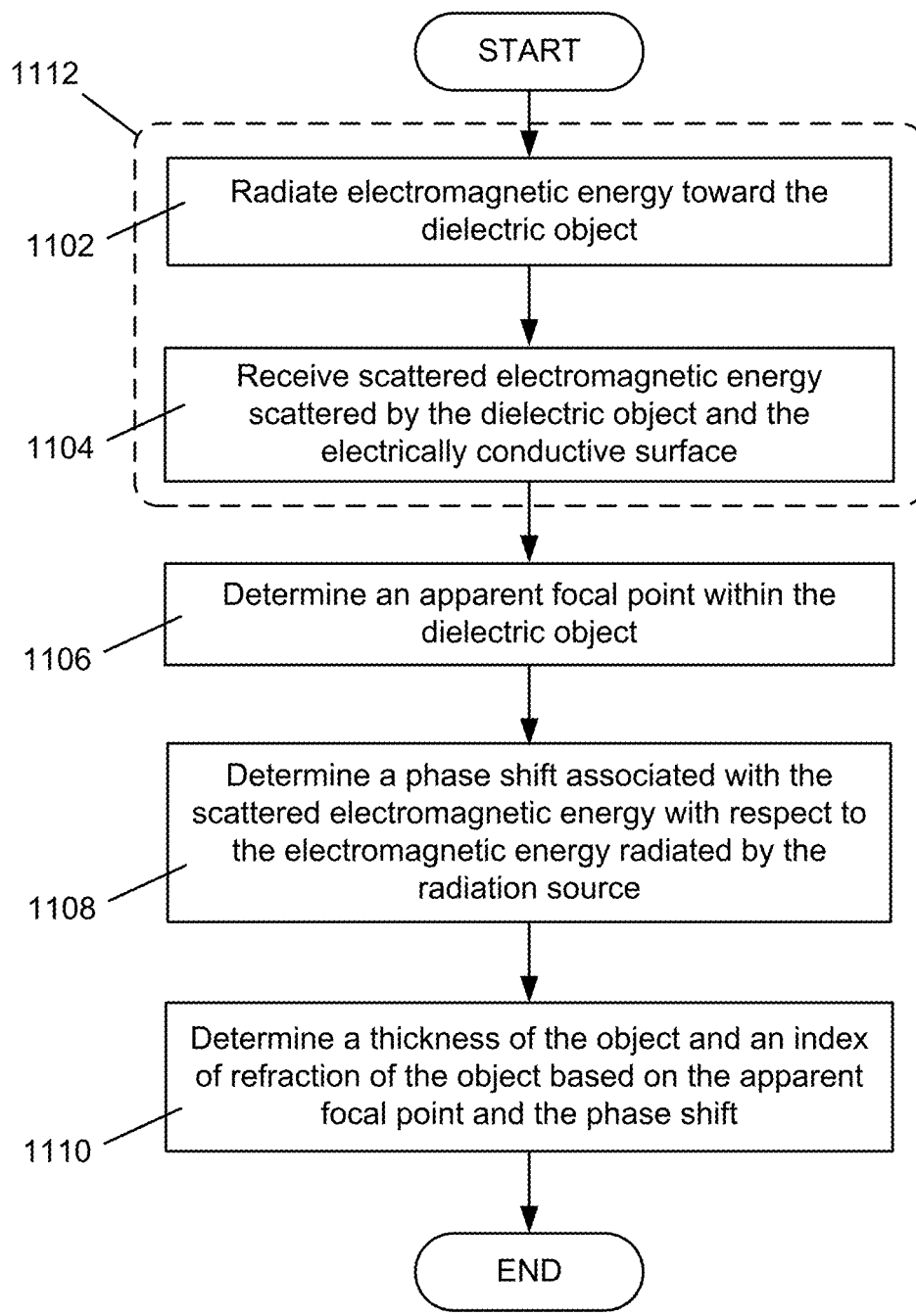
FIG. 11 illustrates an example embodiment of a method of characterizing a dielectric object situated adjacent to an electrically conductive surface.

FIG. 11 illustrates an example embodiment of a method of characterizing a dielectric object situated adjacent to an electrically conductive surface. The method includes radiating 1102 electromagnetic energy toward the dielectric object, and receiving 1104 scattered electromagnetic energy scattered by the dielectric object and the electrically conductive surface. The method further includes determining 1106 an apparent focal point within the dielectric object, determining 1108 a phase shift associated with the scattered electromagnetic energy with respect to the electromagnetic energy radiated by the radiation source, and determining 1110 a thickness of the object and an index of refraction of the object based on the apparent focal point and the phase shift.

Note that the radiate 1102 and receive 1104 steps are grouped 1112 in FIG. 11, which is meant to indicate that the remaining determining steps 1106, 118 and 1110 of the described embodiments may be performed in conjunction with the radiate 1102 and receive 1104 steps.

It will be apparent that one or more embodiments described herein may be implemented in many different forms of software and hardware. Software code and/or specialized hardware used to implement embodiments described herein is not limiting of the embodiments of the invention described herein. Thus, the operation and behavior of embodiments are described without reference to specific software code and/or specialized hardware—it being understood that one would be able to design software and/or hardware to implement the embodiments based on the description herein.

Further, certain embodiments of the example embodiments described herein may be implemented as logic that performs one or more functions. This logic may be hardware-based, software-based, or a combination of hardware-based and software-based. Some or all of the logic may be stored on one or more tangible, non-transitory, computer-readable storage media and may include computer-executable instructions that may be executed by a controller or processor. The computer-executable instructions may include instructions that implement one or more embodiments of the invention. The tangible, non-transitory, computer-readable storage media may be volatile or non-volatile and may include, for example, flash memories, dynamic memories, removable disks, and non-removable disks.

While this invention has been particularly shown and described with references to example embodiments thereof, it will be understood by those skilled in the art that various changes in form and details may be made therein without departing from the scope of the invention encompassed by the appended claims.

What is claimed is:

1. A system for characterizing a dielectric object situated adjacent to an electrically conductive surface, comprising:
   a control subsystem arranged to operate in conjunction with (i) a radiation source configured to radiate electromagnetic energy toward the dielectric object and (ii) a receiver configured to receive scattered electromagnetic energy that is scattered by the dielectric object and the electrically conductive surface, the control subsystem comprising a processor and a memory with computer code instructions stored thereon, the memory operatively coupled to the processor, the control subsystem configured to:
   (i) determine an apparent focal point within the dielectric object, the apparent focal point being a focal point that would occur in the absence of the dielectric object;
   (ii) determine a phase shift associated with the scattered electromagnetic energy with respect to the electromagnetic energy radiated by the radiation source; and
   (iii) determine a thickness of the object and an index of refraction of the object based on the apparent focal point and the phase shift.

2. The system of claim 1, wherein the radiation source is a continuous-wave millimeter-wave source.

3. The system of claim 1, wherein the control subsystem cooperates with an antenna subsystem configured to focus the radiated electromagnetic energy at, within, or proximate to the dielectric object, and to receive the scattered electromagnetic energy scattered by the dielectric object.

4. The system of claim 3, wherein the antenna subsystem comprises a Fresnel reflector aperture antenna.

5. The system of claim 1, wherein to determine the apparent focal point within the dielectric object, the control subsystem is configured to adjust a calculated focus point of the radiated energy to scan through different depths of the dielectric object, and to search for a peak in an amplitude of the scattered electromagnetic energy.

6. The system of claim 5, wherein the control subsystem is further configured to determine a conductive surface location by scanning the calculated focus point away from the dielectric object, and to determine a distance from the conductive surface location to the apparent focal point.

7. The system of claim 1, wherein to determine the thickness of the object, the control subsystem produces a thickness determination as object thickness $$= \frac{c\Delta\Phi\Delta F}{c\Delta\Phi + 2\pi f \Delta F},$$

where c is a velocity of propagation of the radiated electromagnetic energy, f is a frequency of the radiated electromagnetic energy, $\Delta\Phi$ is the phase shift associated with the scattered electromagnetic energy with respect to the electromagnetic energy radiated by the radiation source, and $\Delta F$ is a distance between the apparent focal point within the dielectric object and a true focal point.

8. The system of claim 1, wherein to determine the index of refraction of the object, the control subsystem produces an index of refraction determination as object index of refraction $$= \frac{-c\Delta\Phi}{2\pi f \Delta F},$$

where c is a velocity of propagation of the radiated electromagnetic energy, f is a frequency of the radiated electromagnetic energy, $\Delta\Phi$ is the phase shift associated with the scattered electromagnetic energy with respect to the electromagnetic energy radiated by the radiation source, and $\Delta F$ is a distance between the apparent focal point within the dielectric object and a true focal point.

9. The system of claim 1, wherein the control subsystem determines that an air-to-dielectric interface of the dielectric object is one of (i) parallel to the electrically conductive surface adjacent to the dielectric object and (ii) non-parallel to the electrically conductive surface.

10. The system of claim 9, wherein, when the air-to-dielectric interface of the dielectric object is determined to be non-parallel to the electrically conducting surface, the control subsystem performs an evaluation of the scattered electromagnetic energy as an iterative solution of:

$$E_s(r,\omega) = \int_{r' \in V} G_b(r,\omega) k_b^2 E_T(r',\omega) \chi(r') dr',$$

where $E_s(r,\omega)$ represents a scattered field measured by a receiving antenna located at position r and operating at frequency $\omega$, $G_b(r,\omega)$ indicates background Green's functions, $k_b$ is a wave number; $E_T$ is a total field at a slab region r'∈ (integration range V), and $\chi(r')$ is a contrast variable defined as:

$$\chi(r') = \frac{\varepsilon(r',\omega) - \varepsilon_b(r',\omega)}{\varepsilon_b(r',\omega)},$$

where $\varepsilon(r',\omega)$ represents a dielectric constant at position r, and $\varepsilon_b(r',\omega)$ represents a background dielectric constant.

11. A method of characterizing a dielectric object situated adjacent to an electrically conductive surface, comprising:
by a processor and a memory with computer code instructions stored thereon, the processor and memory operating in conjunction with a radiation source that radiates electromagnetic energy toward the dielectric object and a receiver that receives scattered electromagnetic energy scattered by the dielectric object and the electrically conductive surface, the memory operatively coupled to the processor such that, when executed by the processor, the computer code instructions cause a dielectric object detection system to implement:
(i) determining an apparent focal point within the dielectric object, the apparent focal point being a focal point that would occur in the absence of the dielectric object;
(ii) determining a phase shift associated with the scattered electromagnetic energy with respect to the electromagnetic energy radiated by the radiation source; and
(iii) determining a thickness of the object and an index of refraction of the object based on the apparent focal point and the phase shift.

12. The method of claim 11, further comprising focusing the radiated electromagnetic energy at, within, or proximate to the dielectric object, and to receive the scattered electromagnetic energy scattered by the dielectric object.

13. The method of claim 11, further comprising determining the apparent focal point by adjusting a calculated focus point of the radiated energy to scan through different depths of the dielectric object, and searches for a peak in an amplitude of the scattered electromagnetic energy.

14. The method of claim 13, further comprising determining a conductive surface location by scanning the calculated focus point away from the dielectric object, and determines a distance from the conductive surface location to the apparent focal point.

15. The method of claim 11, further comprising determining the thickness of the object as object thickness $$= \frac{c\Delta\Phi\Delta F}{c\Delta\Phi + 2\pi f \Delta F},$$

where c is a velocity of propagation of the radiated electromagnetic energy, f is a frequency of the radiated electromagnetic energy, $\Delta\Phi$ is the phase shift associated with the scattered electromagnetic energy with respect to the electromagnetic energy radiated by the radiation source, and $\Delta F$ is a distance between the apparent focal point within the dielectric object and a true focal point.

16. The method of claim 11, further comprising determining the index of refraction of the object as object index of refraction $$= \frac{-c\Delta\Phi}{2\pi f \Delta F},$$

where c is a velocity of propagation of the radiated electromagnetic energy, f is a frequency of the radiated electromagnetic energy, $\Delta\Phi$ is the phase shift associated with the scattered electromagnetic energy with respect to the electromagnetic energy radiated by the radiation source, and $\Delta F$ is a distance between the apparent focal point within the dielectric object and a true focal point.

17. The method of claim 11, further comprising determining that an air-to-dielectric interface of the dielectric object is one of (i) parallel to the electrically conductive surface adjacent to the dielectric object and (ii) non-parallel to the electrically conductive surface.

18. The method of claim 17, further comprising, when the air-to-dielectric interface of the dielectric object is determined to be non-parallel to the electrically conducting surface, performing an evaluation of the scattered electromagnetic energy as an iterative solution of:

$$E_s(r,\omega) = \int_{r'\in V} G_b(r,\omega) k_b^2 E_T(r',\omega) \chi(r') dr',$$

where $E_s(r,\omega)$ represents a scattered field measured by a receiving antenna located at position r and operating at frequency $\omega$, $G_b(r,\omega)$ indicates background Green's functions, $k_b$ is a wave number; $E_T$ is a total field at a slab region r'∈ (integration range V), and $\chi(r')$ is a contrast variable defined as:

$$\chi(r') = \frac{\varepsilon(r',\omega) - \varepsilon_b(r',\omega)}{\varepsilon_b(r',\omega)},$$

where $\varepsilon(r',\omega)$ represents a dielectric constant at position r, and $\varepsilon_b(r',\omega)$ represents a background dielectric constant.

19. A non-transitory computer-readable medium with computer code instruction stored thereon, the computer code instructions, when executed by a processor, cause a dielectric object detection system to:
determine an apparent focal point within the dielectric object, based on electromagnetic energy scattered by the dielectric object and the electrically conductive surface, the apparent focal point being a focal point that would occur in the absence of the dielectric object;
determine a phase shift associated with the scattered electromagnetic energy with respect to the electromagnetic energy radiated by a radiation source emitting the electromagnetic energy; and
determine a thickness of the object and an index of refraction of the object based on the apparent focal point and the phase shift.

20. The non-transitory computer-readable medium of claim 19, wherein the computer code instructions, when executed by the processor, further cause the dielectric object detection system to adjust a calculated focus point of the radiated energy to scan through different depths of the dielectric object, and searches for a peak in an amplitude of the scattered electromagnetic energy.

* * * * *